United States Patent [19]

Sweet

[11] 4,238,485

[45] Dec. 9, 1980

[54] NOVEL PHARMACEUTICAL COMPOSITIONS

[75] Inventor: Charles S. Sweet, Lansdale, Pa.

[73] Assignee: Merck & Co., Inc., Rahway, N.J.

[21] Appl. No.: 88,900

[22] Filed: Oct. 29, 1979

Related U.S. Application Data

[63] Continuation of Ser. No. 966,521, Dec. 4, 1978, abandoned, which is a continuation of Ser. No. 734,702, Oct. 21, 1976, abandoned, which is a continuation-in-part of Ser. No. 554,373, Mar. 3, 1975, abandoned, which is a continuation-in-part of Ser. No. 497,961, Aug. 16, 1974, abandoned.

[51] Int. Cl.³ .................. A61K 27/00; A61K 31/54; A61K 31/445
[52] U.S. Cl. .................. 424/246; 424/248.51; 424/267
[58] Field of Search .................. 424/246, 248.51

[56] References Cited

U.S. PATENT DOCUMENTS

| | | | |
|---|---|---|---|
| 3,655,663 | 4/1972 | Wasson | 424/248 |
| 3,718,647 | 2/1973 | Weinstock et al. | 424/248.51 |
| 3,729,469 | 4/1973 | Wasson | 424/248 |
| 3,812,182 | 5/1974 | Weinstock et al. | 424/248.51 |

OTHER PUBLICATIONS

Morgan et al. (1), The Medical Journal of Australia, 2, pp. 309–312 (1972).
Morgan et al. (2), Postgraduate Medical Journal, 50, pp. 253–259 (May 1974).
Chalmers et al., Lancet 2, pp. 328–331 (1976).

*Primary Examiner*—Stanley J. Friedman
*Attorney, Agent, or Firm*—Daniel T. Szura

[57] ABSTRACT

Compositions containing substituted 1,2,5-thiadiazole β-blocking agent and pyrazine and/or thiazide diuretic, and a method of treating hypertensive animals are disclosed.

13 Claims, No Drawings

NOVEL PHARMACEUTICAL COMPOSITIONS

CROSS REFERENCE TO RELATED APPLICATIONS

This is a continuation, of co-pending U.S. application Ser. No. 966,521 filed Dec. 4, 1978 now abandoned, which in turn is a continuation of U.S. application Ser. No. 734,702, filed Oct. 21, 1976, now abandoned which in turn is a continuation-in-part of U.S. application Ser. No. 554,373, filed Mar. 3, 1975 now abandoned, which in turn is a continuation-in-part of U.S. application Ser. No. 497,961 filed Aug. 16, 1974 now abandoned.

BACKGROUND OF THE INVENTION

Diuretics such as the thiazides and pyrazines are useful as antihypertensive agents. However, these diuretics tend to increase circulating plasma renin levels. This increase in renin may be undesirable since it acts to reduce the antihypertensive effect of the diuretic.

$\beta$-adrenergic blocking agents are another class of drugs which are effective in long term treatment of hypertension. Propranalol, a $\beta$-adrenergic blocking agent, has been found to inhibit renal renin secretion in man and in animals [New England Journal of Medicine 287, 1209–1213 (1972)] Pindolol, another $\beta$-adrenergic blocking agent, has been found to have antihypertensive effect when administered alone and in combination with a thiazide diuretic [The Medical Journal of Australia 2, 309–312, (1972)]. The effect on hypertension of a combination of large doses of 4 different $\beta$-blocking agents (including a substituted 1,2,5-thiadiazole) with a thiazide diuretic, has also been reported (Postgraduate Medical Journal 50, 253–259, May, 1974).

It has been discovered that administration of a particular combination of a substituted 1,2,5 thiadiazole $\beta$-adrenergic blocking agent and said diuretic to a hypertensive animal (1) enhances the antihypertensive activity of the diuretic and (2) reduces the severity of potassium loss due to the diuretic.

SUMMARY OF THE INVENTION

Composition comprising (1) a substituted 1,2,5 thiadiazole $\beta$-blocking agent and (2) a thiazide and/or pyrazine diuretic; and a method of treating a hypertensive animal.

DESCRIPTION OF THE PREFERRED EMBODIMENTS

An embodiment of the present invention are compositions containing:

(A) $\beta$-blocking agents selected from:
(i) compounds having the formula

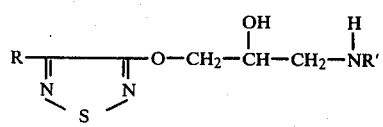

wherein R is selected from hydrogen, halogen, $C_3$-$C_6$ cycloalkyl, $C_1$-$C_4$ alkyl, $C_2$-$C_4$ alkenyl, phenyl, substituted phenyl, $C_1$-$C_5$ alkoxy, heterocycle, $C_1$-$C_4$ alkylcarbamoyl, carbamoyl and $R^2$—L—$R^3$— wherein $R^2$ is selected from $C_1$-$C_3$ alkyl, phenyl and substituted phenyl, L is selected from oxygen and sulfur and $R^3$ is methyl or ethyl; and R' is selected from $C_1$-$C_{10}$ alkyl, $C_2$-$C_6$ alkynyl, $C_2$-$C_4$ alkenyl, $C_3$-$C_6$ cycloalkyl, $C_1$-$C_4$ alkylthio, and heterocycle.

(ii) non-toxic pharmaceutically acceptable salts of (i); and
(iii) mixtures containing (i) and (ii); and (B.) diuretic selected from:
(a.) thiazides and their pharmaceutically acceptable salts
(b.) amiloride and its pharmaceutically acceptable salts and
(c.) mixtures of (a) and (b).

The $\beta$-blocking agents of the Formula I include the individual optical isomers as well as the racemate. More preferred Formula I compounds and salts are those wherein R is hydrogen; halogen such as chlorine, bromine, fluorine and the like; alkyl such as methyl, ethyl, propyl, t-butyl and the like; alkenyl such as vinyl, allyl, methallyl and the like: $R^2$—L—$R^3$— radical wherein $R^2$ is alkyl such as methyl, ethyl, propyl; phenyl or substituted phenyl wherein the substituents are selected from the group consisting of halogen such as chlorine, bromine, fluorine and the like, hydroxy, alkyl such as methyl, ethyl, propyl and the like, or alkoxy such as methoxy, ethoxy, propoxy and the like; L is oxygen or sulfur and $R^3$ is alkyl such as methyl and ethyl; carbamoyl; alkylcarbamoyl wherein the alkyl moiety is represented by methyl, ethyl, isopropyl, butyl and the like; cycloalkyl such as cyclopropyl, cyclobutyl, cyclopentyl, cyclohexyl and the like; alkoxy such as methoxy, ethoxy, propoxy, isopropoxy, butoxy, pentoxy and the like; phenyl or substituted phenyl wherein the substituents are selected from the group consisting of one or more halogen such as chlorine, fluorine and the like, alkyl having from 1 to 3 carbons, and alkoxy having from 1 to 3 carbons, aralkyl wherein the alkyl moiety has from 1 to 4 carbons and the aryl moiety can be unsubstituted or substituted with one or more halogen such as chlorine, fluorine, bromine and the like, alkyl having from 1 to 3 carbons, or alkoxy having from 1 to 3 carbons; and a heterocyclic moiety such as aziridinyl, azetidinyl, pyrrolidyl, piperidyl, hexahydroazepineo, morpholino, piperidino, thiazolidinyl, p-thiazinyl, piperazinyl, thienyl, furyl and the like; R' is alkyl having from 1 up to about 10 carbons, preferably 1 to 6 carbons and more preferably from 3 to 6 carbons such as isopropyl, tert-butyl, 2,2-dimethylpropyl, hexyl and the like; alkenyl such as allyl, vinyl, methalkyl and the like; or alkynyl groups having from 2 to 6 carbons, such as —C≡CH, propynyl, butynyl, propargyl, hexynyl and the like; substituted alkyl wherein the substituents are selected from the group consisting of hydroxy and halogen such as chlorine, bromine and the like; carboxy; alkoxy; alkylthio wherein the alkyl moiety contains from 1 to 4 carbons; cycloalkyl such as cyclopropyl, cyclohexyl, cyclopentyl and the like; and a heterocyclic group such as pyrrolidinyl, piperazinyl, morpholino, thiazolidinyl, thienyl, furyl, thiazinyl and the like.

Formula I compounds where R is morpholino, piperidino or hydroxypiperidino are more preferred—and particularly preferred are the Formula I compounds where R is morpholino, piperidino, hydroxypiperidino and R' is $C_1$-$C_{10}$ alkyl.

Representative Formula I compounds and their salts which are useful in this invention are:
3-chloro-4-(3-t-butylamino-2-hydroxypropoxy)-1,2,5-thiadiazole (+)-3-chloro-4-(3-t-butylamino-2-hydroxypropoxy)-1,2,5-thiadiazole hydrocyloride
3-bromo-4-(3-t-butylamino-2-hydroxypropoxy)-1,2,5-thiadiazole
(−)-3-bromo-4-(3-t-butylamino-2-hydroxypropoxy)-1,2,5-thiadiazole hydrochloride
3-(4-hydroxypiperidino)-4-(3-t-butylamino-2-hydroxypropoxy)-1,2,5-thiadiazole
3-morpholino-4-(3-n-hexylamino-2-hydroxypropoxy)-1,2,5-thiadiazole hydrogen maleate
(30)-3-morpholino-4-(3-t-butylamino-2-hydroxypropoxy)-1,2,5-thiadiazole hydrogen maleate
(−)-3-morpholino-4-(3-t-butylamino-2-hydroxypropoxy)-1,2,5-thiadiazole hydrogen maleate
3-morpholino-4-(3-t-butylamino-2-hydroxypropoxy)-1,2,5-thiadiazole hydrochloride
3-N-t-butylcarbamoyl-4-(3-t-butylamino-2-hydroxypropoxy)-1,2,5-thiadiazole
(+)-3-N-t-butylcarbamoyl-4-(3-t-butylamino-2-hydroxypropoxy)-1,2,5-thiadiazole hydrochloride
(−)-3-N-t-butylcarbamoyl-4-(3-t-butylamino-2-hydroxypropoxy)-1,2,5-thiadiazole hydrochloride
3-N-isopropylcarbamoyl-4-(3-isopropylamino-2-hydroxypropoxy)-1,2,5-thiadiazole
(+)-3-N-isopropylcarbamoyl-4-(3-isopropylamino-2-hydroxypropoxy)-1,2,5-thiadiazole hydrochloride
(−)-3-N-isopropylcarbamoyl-4-(3-isopropylamino-2-hydroxypropoxy)-1,2,5-thiadiazole hydrochloride
3-morpholino-4-(3-t-butylamino-2-hydroxypropoxy)-1,2,5-thiadiazole benzoate
3-chloro-4-(3-isopropylamino-2-hydroxypropoxy)-1,2,5-thiadiazole
3-bromo-4-(3-isopropylamino-2-hydroxypropoxy)-1,2,5-thiadiazole
(+)-3-chloro-4-(3-isopropylamino-2-hydroxypropoxy)-1,2,5-thiadiazole
3-methyl-4-(3-n-butylamino-2-hydroxypropoxy)-1,2,5-thiadiazole
3-ethoxy-4-(3-sec-butylamino-2-hydroxypropoxy)-1,2,5-thiadiazole and the like.

Especially preferred Formula I compounds are those in which R is halogen, alkyl, alkoxy, phenyl, benzyl, morpholino, piperazino and piperidino and R' is alkyl, preferably $C_3$–$C_6$. A most preferred Formula I compound is one where R is morpholino, R' is t-butyl, and more particularly the (−)isomer and pharmaceutically acceptable salts thereof, especially the hydrogen maleate.

The pharmaceutically acceptable salts of Formula I compounds are included as useful compounds in the present invention. Any non-toxic, pharmaceutically acceptable salt of Formula I compounds may be used. Representative examples of these pharmaceutically acceptable salts are the hydrohalides, e.g., hydrochlorides, hydrobromides, hydroiodides; the phosphates, sulfates, oxalates, lactates, malates, maleates, formates, acetates, succinates, tartrates, salicylates, citrates, phenylacetates, benzoates, p-toluenesulfonates and other salts such as those that provide relatively insoluble products that afford a slow release of the active material, for example, a 1,1'-methylene-bis(2-hydroxy-3-naphthoate) and the like.

The β-blocking agents of Formula I and methods for their preparation are described in U.S. Pat. No. 3,655,663, U.S. Pat. No. 3,729,469, U.S. Pat. No. 3,657,237, U.S. Pat. No. 3,718,647 and U.S. Pat. No. 3,812,182. To the extent necessary, the disclosure of said patents is incorporated herein by reference.

The diuretics used in the present invention include (a) thiazides and their non-toxic pharmaceutically acceptable salts (b) pyrazine and its non-toxic pharmaceutically acceptable salts, and (c) mixtures of (a) and (b).

The thiazides comprise a 1,2,4 benzothiazine class of compounds. They include compounds such as flumethiazide, benzthiazide, cyclopenthiazide, cyclothiazide, trichloromethiazide, benzhydroflumethiazide, methylcyclothiazide, polythiazide, thiabutazide, and the like and their non-toxic, pharmaceutically acceptable salts.

Preferred thiazides are those having the following formulae:

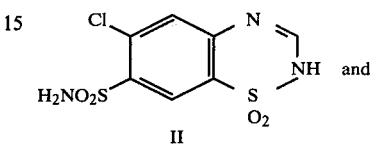

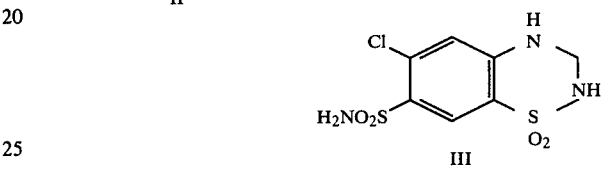

and their pharmaceutically acceptable salts.

The Formula II compound is chlorothiazide and the Formula III compound is hydrochlorothiazide. Salts of the Formula II and III compounds include those of alkali metals, especially sodium.

The thiazide diuretics, their use and methods for their preparation are described in U.S. Pat. Nos. 2,809,194, 3,025,292, 2,937,169, 3,164,588 and 3,043,840. The information in these patents is incorporated herein by reference.

The pyrazine diuretic has the formula

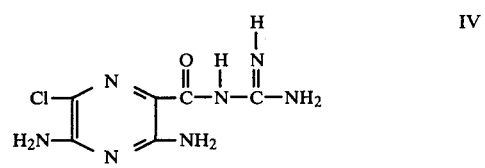

The Formula IV compound is amiloride. The compound and its preparation are described in Belgian Pat. No. 639,386. Amiloride is also useful as a non-toxic pharmaceutically acceptable salt of inorganic acid, e.g., hydrohalo acid, phosphorus acid, sulfuric acid and the like, and organic acid e.g., citric, tartaric, maleic, sulfonic, phosphonic, malic, acetic, and the like. A most preferred salt of amiloride is the hydrochloride dihydrate.

Combinations containing thiazide and pyrazine diuretics are also useful. The weight ratios of the diuretics in these combinations can be varied. Generally weight ratios of diazine: thiazide from 1:1 to 1:10 are useful and a weight ratio of 1:10 is particularly useful. In a preferred combination the diazine is amiloride hydrochloride (or its dihydrate) and the thiazide hydrochlorothiazide—and in a most preferred combination the weight ratio of said amiloride; said hydrochlorothiazide is 1:10. These combinations are disclosed in U.S. Pat. No. 3,781,430.

The compositions of the present invention are administered in dose quantities of β-adrenergic blocking agent:diuretic in weight ratio of from about 1:15 to about 24:1, preferably about 1:12 to about 4:1 and more preferably about 1:1 to about 4:1 and most preferably about 1:1 to about 1:10; a 1:1.25–1:5 ratio range is especially preferred. The amount of β-adrenergic blocking agent and diuretic administered is varied. Generally, the β-blocking agent is administered in quantities ranging from 1–12 mg. per kilogram of animal body weight while the diuretic is administered in quantities ranging from about 0.5–15 mg. per kilogram of animal body weight. A preferable administration quantity range for the β-blocking agent is about 1–8 mg./kg/day and for the diuretic about 1–10 mg./kg./day. The present compositions are useful for treating hypertension in animals (patients) to effect a decrease in blood pressure. These compositions are administered in varying dosages and for various periods of time as the treatment requires.

It is to be understood, however, that the specific dose level for any particular patient will depend upon a variety of factors including the activity of the specific compound employed, the age, body weight, general health, sex, diet, time of administration, rate of excretion, drug combination and the severity of the disease undergoing therapy.

The compositions of the present invention may be administered in any acceptable and recognized manner. They are preferably administered orally in an acceptable dosage form. The compounds may be combined in a capsule. The compositions may be provided in the form of tablets,; said tablets may include other ingredients which are ordinarily used to facilitate tablet formation, palatability, etc. The compositions may likewise be dissolved or dispersed in a pharmaceutically acceptable carrier for administration in a fluid form.

The following examples illustrate but do not limit the preparation of the various compositions of the invention.

TABLE I

| Ingredients | Ex. 1 | Ex. 2 | Ex. 3 | Ex. 4 | Ex. 5 | Ex. 6 |
|---|---|---|---|---|---|---|
| 3-morpholino-4-(3-t-butylamino-2-hydroxypropoxy)-1,2,5-thiadiazole | 10 | 10 | 10 | 5 | 5 | 5 |
| Hydrochlorothiazide | 10 | 25 | 50 | 10 | 25 | 50 |
| Starch USP Corn | 124 | 114 | 109 | 99 | 84 | 80 |
| Microcrystalline Cellulose | 134 | 129 | 109 | 85 | 85 | 54 |
| Magnesium Stearate | 2 | 2 | 2 | 1 | 1 | 1 |
| TOTAL (mg./tablet) | 280 | 280 | 280 | 200 | 200 | 200 |

3-morpholino-4-(3-t-butylamino-2-hydroxypropoxy)-1,2,5-thiadiazole, hydrochlorothiazide, part of the corn starch and microcrystalline cellulose are mixed together, milled and granulated with part of the corn starch as starch paste. The granulated mass is wet-sized, dried, dry milled, and blended with the remaining corn starch and microcrystalline cellulose, lubricated with magnesium stearate, and compressed to tablets.

Equivalent amounts of chlorothiazide or its sodium salt may be substituted for the hydrochlorothiazide in the Table I formulation to prepare corresponding compositions.

When other β-adrenergic blocking agents such as 3-chloro-4-(3-t-butylamino-2-hydroxypropoxy)-1,2,5-thiadiazole, 3-(4-hydroxypiperidino)-4-(3-t-butylamino-2-hydroxypropoxy)-1,2,5-thiadiazole, 3-piperazino-4-(3-t-butylamino-2-hydroxypropoxy)-1,2,5-thiadiazole, 3-piperidino-4-(3-t-butylamino-2-hydroxypropoxy)-1,2,5-thiadiazole, 3-N-isopropylcarbamoyl-4-(3-t-butylamino-2-hydroxypropoxy)-1,2,5-thiadiazole, 3-N-isopropylcarbamoyl-4-(3-isopropylamino-2-hydroxypropoxy)-1,2,5-thiadiazole, 3-methyl-4-(3-t-butylamino-2-hydroxypropoxy)-1,2,5-thiadiazole, 3-ethoxy-4-(3-t-butylamino-2-hydroxypropoxy)-1,2,5-thiadiazole or representative salt thereof is substituted for 3-morpholino-4-(3-t-butylamino-2-hydroxypropoxy)-1,2,5-thiadiazole, there is obtained the corresponding composition.

TABLE II

| Ingredients | Ex. 7 | Ex. 8 | Ex. 9 | Ex. 10 | Ex. 11 | Ex. 12 |
|---|---|---|---|---|---|---|
| 3-morpholino-4-(3-t-butylamino-2-hydroxypropoxy)-1,2,5-thiadiazole hydrogen maleate | 10 | 10 | 10 | 5 | 5 | 5 |
| Hydrochlorothiazide | 10 | 25 | 50 | 10 | 25 | 50 |
| Starch USP Corn | 124 | 114 | 109 | 99 | 84 | 80 |
| Microcrystalline Cellulose | 134 | 129 | 109 | 85 | 85 | 54 |
| Magnesium Stearate | 2 | 2 | 2 | 1 | 1 | 1 |
| TOTAL (mg./tablet) | 280 | 280 | 280 | 200 | 200 | 200 |

3-morpholino-4-(3-t-butylamino-2-hydroxypropoxy)-1,2,5-thiadiazole hydrogen maleate, hydrochlorothiazide, part of the corn starch and microcrystalline cellulose are mixed together, milled and granulated with part of the corn starch as starch paste. The granulated mass is wet-sized, dried, dry milled, and blended with the remaining corn starch and microcrystalline cellulose, lubricated with magnesium stearate, and compressed into tablets.

Corresponding compositions are prepared when an equivalent amount of amiloride or its hydrochloride dihydrate is substituted for hydrochlorothiazide in Table II.

When other optically active β-adrenergic blocking agents such as (−)-3-chloro-4-(3-t-butylamino-2-hydroxypropoxy)-1,2,5-thiadiazole hydrochloride, (−)-3-(4-hydroxypiperidino)-4-(3-t-butylamino-2-hydroxypropoxy)-1,2,5-thiadiazole hydrochloride, (−)-3-piperidino-4-(3-t-butylamino-2-hydroxypropoxy)-1,2,5-thiadiazole hydrogen maleate, (−)-3-N-t-butylcarbamoyl-4-(3-t-butylamino-2-hydroxypropoxy)-1,2,5-thiadiazole hydrochloride, (−)-3-methyl-4-(3-t-butylamino-2-hydroxypropoxy)-1,2,5-thiadiazole hydrochloride, (−)-3-ethoxy-4-(3-t-butylamino-2-hydroxypropoxy)-1,2,5-thiadiazole hydrochloride or (−)-3-chloro-4-(3-t-butylamino-2-hydroxypropoxy)-1,2,5-thiadiazole is substituted for 3-morpholino-4-(3-t-butylamino-2-hydroxypropoxy)-1,2,5-thiadiazole hydrogen maleate, there is obtained the corresponding composition.

TABLE III

| Ingredients | Ex. 13 | Ex. 14 | Ex. 15 | Ex. 16 | Ex. 17 | Ex. 18 |
|---|---|---|---|---|---|---|
| 3-morpholino-4-3-t-butylamino-2-hydroxypropoxy)-1,2,5-thiadiazole hydrogen maleate (racemate) | 10 | 10 | 10 | 5 | 5 | 5 |
| Hydrochlorothiazide | 10 | 25 | 50 | 10 | 25 | 50 |
| Starch USP Corn | 124 | 114 | 109 | 99 | 84 | 80 |
| Microcrystalline Cellulose | 134 | 129 | 109 | 85 | 85 | 54 |
| Magnesium Stearate | 2 | 2 | 2 | 1 | 1 | 1 |
| TOTAL (mg./tablet) | 280 | 280 | 280 | 200 | 200 | 200 |

(3-morpholino-4-(3-t-butylamino-2-hydroxypropoxy)-1,2,5-thiadiazole hydrogen maleate (racemate), hydralazine, part of the corn starch and microcrystalline cellulose are mixed together, milled and granulated with part of the corn starch as starch paste. The granulated mass is wet-sized, dried, dry milled, and blended with the remaining corn starch and microcrystalline cellulose, lubricated with magnesium stearate, and compressed into tablets.

A mixture containing hydrochlorothiazide and amiloride hydrochloride dihydrate are substituted for hydrochlorothiazide in Table III to prepare corresponding compositions.

When other optically active β-adrenergic blocking agents such as racemic 3-chloro-4-(3-t-butylamino-2-hydroxypropoxy)-1,2,5-thiadiazole hydrochloride, (−)-3-(4-hydroxypiperidino)-4-(3-t-butylamino-2-hydroxypropoxy)-1,2,5-thiadiazole citrate, (+)-3-piperidino-4-(3-t-butylamino-2-hydroxypropoxy)-1,2,5-thiadiazole hydrochloride, racemic 3-morpholino-4-(3-t-butylamino-2-hydroxypropoxy)-1,2,5-thiadiazole hydrobromide, (+)-3-N-t-butylcarbamoyl-4-(3-t-butylamino-2-hydroxypropoxy)-1,2,5-thiadiazole hydrochloride, (−)-3-methyl-4-(3-t-butylamino-2-hydroxypropoxy)-1,2,5-thiadiazole acetate, (+)-3-ethoxy-4-(3-t-butylamino-2-hydroxypropoxy)-1,2,5-thiadiazole phosphate, or (+)-3-chloro-4-(3-t-butylamino-2-hydroxybutoxy)-1,2,5-thiadiazole hydrochloride is substituted for racemic 3-morpholino-4-(3-t-butylamino-2-hydroxypropoxy)-1,2,5-thiadiazole hydrogen maleate, with the hydrochlorothiazide or mixed hydrochlorothiazide/amiloride HCl.2H₂O corresponding compositions are obtained.

The effect of the compositions of the present invention on blood pressure and plasma potassium was determined by an in vivo procedure utilizing adult beagle dogs in which hypertension was produced by surgical modification of the kidney. The blood pressure and plasma potassium level of these hypertensive dogs were measured over a number of days before and after (twice a day) oral administration (in gelatin capsules) of hydrochlorothiazide (HCTZ) and a combination of HCTZ and (−)-3-morpholino-4-(3-t-butylamino-2-hydroxypropoxy)-1,2,5-thiadiazole hydrogen maleate (MTHM). The results obtained from a statistically designed set of experiments, using the aforesaid procedure, are tabulated below:

TABLE A
EFFECT ON BLOOD PRESSURE AND PLASMA POTASSIUM

| Test | Treatment | No. Of Dogs | Days Of Treatment | Plasma[1] Potassium | Blood[2] Pressure |
|---|---|---|---|---|---|
| A | 1 Control | 5 | — | 4.2 | 140 |
|   | 2 HCTZ-10 mg/kg/day | 5 | 2 | 3.4 | 122 |
|   | 3 HCTZ-10 mg/kg/day | 5 | 4 | 3.6 | 129 |
| D | 1 Control | 5 | — | 4.3 | 132 |
|   | 2 HCTZ-10 mg/kg/day + MTHM-2.0 mg/kg/day | 5 | 2 | 4.1 | 114 |
|   | 3 HCTZ-10 mg/kg/day + MTHM-2.0 mg/kg/day | 5 | 4 | 4.1 | 105 |
| B | 1 Control (lactose) | 4 | — | — | 126 |
|   | 2 MTHM-1.0 mg/kg/day | 4 | 2 | — | 128 |
|   | MTHM-10 mg/kg/day | 4 | 4 | — | 133 |
|   | 3 MTHM-4.0 mg/kg/day | 4 | 2 | — | 137 |
|   | MTHM-4.0 mg/kg/day | 4 | 4 | — | 141 |
| C | 1 Control | 6 | 3 | 4.5 | — |
|   | MTHM-2.0 mg/kg/day | 12 | 3 | 5.0 | — |

[1] millequivalents/liter
[2] mean arterial in mm/Hg

Comparable results were obtained when comparing effect on blood pressure and plasma potassium of 2.5 mg./kg/day HCTZ with 2.5 mg./kg/day HCTZ+2 mg./kg/day MTHM and 2.5 mg./kg/day HCTZ+8 mg./kg/day MTHM. The data presented in Table A, clearly shows that the substituted thiadiazole substantially enhances (1) the antihypertensive effect of hydrochlorothiazide and (20 reduces the severity of potassium loss produced by hydrochlorothiazide.

Other combinations and dosages which have been studied are MTHM/HCTZ at 1.0/2.5, 4.0/10.0 and 8.0/10.0 mg/kg/day; and MTHM/HCTZ/amiloride hydrochloride dihydrate at 1.0/2.5/0.25, 4.0/10.0/1.0, 8.0/10.0/1.0, and 10.0/25/2.5 mg/kg/day. Tablets containing 10 mg MTHM/25 mg HCTZ or 10 mg MTHM/25 mg HCTZ/2.5 mg amiloride hydrochloride dihydrate administered twice a day, orally, to hypertensive humans have been shown to be effective.

In addition to blood pressure reduction and plasma potassium level maintained the HCTZ/MTHM compositions were also found to reduce circulating renin levels.

Analogous results are obtained for other compositions of the present invention as disclosed herein. Claims to the invention follow.

What is claimed is:

1. Composition useful for treating hypertension comprising:
   (A) β-blocking agent selected from:
      (i) compounds having the formula

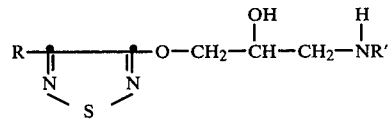

wherein R is morpholino or piperidino and R' is $C_3-C_6$ alkyl,
      (ii) non-toxic pharmaceutically acceptable salts of (i); and
      (iii) mixtures containing (i) and (ii); and
   (B) diuretic selected from a 1,2,4 benzothiadiazine and
   a pharmaceutically acceptable salt thereof
wherein the weight ratio of (A.):(B.) is about 1:1 to about 1:10.

2. A composition of claim 1 wherein said thiazide is selected from chlorothiazide, alkali metal salts of chlorothiazide, and hydrochlorothiazide.

3. A composition of claim 2 wherein R is morpholino or piperidino and R' is isopropyl or t-butyl.

4. Composition of claim 3 wherein R is morpholino.

5. Composition of claim 4 wherein said diuretic is hydrochlorothiazide.

6. Composition of claim 5 wherein R' is t-butyl.

7. Composition of claim 6 wherein said β-blocking agent is said (ii) salt of the (i) (−) isomer.

8. Composition of claim 7 wherein said (ii) is the hydrogen maleate.

9. Composition of claim 8 wherein said ratio range 1:1.25–1:5.

10. Composition of claim 8 in tablet form containing 5 or 10 mg of (A.) and 10, 25 or 50 mg of (B.).

11. Composition of claim 8 in tablet form containing 10 mg of (A.) and 25 mg of (B.).

12. The composition of claim 1 wherein said 1,2,4 benzothiadazine is flumethiazide, benzthiazide, cyclopenthiazide, cyclothiazide, trichloromethiazide, benzhydroflumethiazide, methylcyclothiazide, polythiazide, thiabutazide, hydrochlorothiazide, chlorothiazide or a pharmaceutically acceptable salt thereof.

13. A method of treating a hypertensive animal to reduce blood pressure which comprises administration of a blood pressure reducing amount of a composition of claim 1.

* * * * *